(12) United States Patent
Wei et al.

(10) Patent No.: US 11,191,870 B2
(45) Date of Patent: Dec. 7, 2021

(54) GEL OF SODIUM HYALURONATE CROSS-LINKED BY POLYETHYLENE GLYCOL EPOXY DERIVATIVE FOR INJECTION AND PREPARATION METHOD THEREOF

(71) Applicant: JENKEM TECHNOLOGY CO., LTD. (BEIJING), Beijing (CN)

(72) Inventors: Zhen Wei, Beijing (CN); Meina Lin, Beijing (CN); Xuan Zhao, Beijing (CN)

(73) Assignee: JENKEM TECHNOLOGY CO., LTD., Beijing (CN)

( * ) Notice: Subject to any disclaimer, the term of this patent is extended or adjusted under 35 U.S.C. 154(b) by 167 days.

(21) Appl. No.: 16/473,479

(22) PCT Filed: Dec. 26, 2017

(86) PCT No.: PCT/CN2017/118542
§ 371 (c)(1),
(2) Date: Jun. 25, 2019

(87) PCT Pub. No.: WO2018/121510
PCT Pub. Date: Jul. 5, 2018

(65) Prior Publication Data
US 2020/0147262 A1 May 14, 2020

(30) Foreign Application Priority Data

Dec. 29, 2016 (CN) .......................... 201611246123.9
Dec. 21, 2017 (CN) .......................... 201711399574.0

(51) Int. Cl.
*A61L 27/20* (2006.01)
*C08G 65/10* (2006.01)
*C08J 3/24* (2006.01)
*C08J 3/075* (2006.01)

(52) U.S. Cl.
CPC .............. *A61L 27/20* (2013.01); *C08G 65/10* (2013.01); *C08J 3/24* (2013.01); *A61L 2430/34* (2013.01); *C08J 3/075* (2013.01); *C08J 2305/08* (2013.01); *C08J 2471/02* (2013.01)

(58) Field of Classification Search
CPC ........ A61L 27/20; A61L 2430/34; C08J 3/24; C08J 3/075; C08G 65/10
USPC ......................................................... 514/54
See application file for complete search history.

(56) References Cited

PUBLICATIONS

Lee et al. Mechanical Improvement of Hyaluronic Acid (HA) Hydrogels and Incorporation of Polyethylene Glycol (PEG). Biometaerials, 37 (2015), Article 495 (Year: 2015).*
Dimonie et al. α,w-Bis(2,3-epoxypropyl)oligooxyethylene-based crosslinked resins as solid-liquid phase-transfer catalysts. Die Angewandte Makromolekuiare Chemie 209 (1993) 55-61. (Year: 1993).*
Gu et al. Synthesis of Glycol Diglycidyl Ethers Using Phase-Transfer Catalysis. Synthesis Jun./Jul. 1985, 649-651. (Year: 1985).*

* cited by examiner

*Primary Examiner* — Yih-Horng Shiao
(74) *Attorney, Agent, or Firm* — Platinum Intellectual Property LLP (57) ABSTRACT

The present invention discloses polyglycol epoxide cross-linked sodium hyaluronate gel for injection and a preparation method thereof. A polyglycol epoxide is a compound with single molecular weight preferably; a plurality of ether bonds are present in the molecule of the polyglycol epoxide, the water solubility is good, and thus, the polyglycol epoxide is more easily subjected to a crosslinking reaction with polysaccharides; and meanwhile, polyglycol is relatively easy in adjustment of the number of repeating units and relatively easy in control of length, and thus, the sodium hyaluronate gel prepared by taking the polyglycol epoxide as a crosslinker is relatively easy in regulation and control of properties. The crosslinked sodium hyaluronate gel is low in toxicity, little in residual, small in squeezing and pushing force, good in shaping performance, good in enzyme resistance and long in in-vivo retention time. The present invention further discloses a mild crosslinker deactivation technology. Unreacted epoxide groups in the gel are subjected to a hydrolysis reaction in a carbonate buffer system with a pH of 8-9, so that the difficulty of impurity removal of the crosslinked sodium hyaluronate gel can be effectively lowered, and the problem of toxicity in the prior art due to the fact that BDDE is used in a crosslinking method is avoided.

3 Claims, 2 Drawing Sheets

GEL OF SODIUM HYALURONATE CROSS-LINKED BY POLYETHYLENE GLYCOL EPOXY DERIVATIVE FOR INJECTION AND PREPARATION METHOD THEREOF

RELATED APPLICATIONS

This application is a United States National Stage Application filed under 35 U.S.C. 371 of PCT Patent Application Serial No. PCT/CN2017/118542, filed Dec. 26, 2016, which claims Chinese Patent Application Serial No. CN 201611246123.9, filed Dec. 29, 2016 and Chinese Patent Application Serial No. CN 201711399574.0, filed Dec. 21, 2017, the disclosure of all of which are hereby incorporated by reference in their entirety.

TECHNICAL FIELD

The present invention relates to the technical field of sodium hyaluronate gel and particularly relates to polyglycol epoxide crosslinked sodium hyaluronate gel and a preparation method thereof.

BACKGROUND

Hyaluronic acid (HA) is a linear-chain macromolecular viscose polysaccharide prepared from diose units, i.e., glucuronic acid and acetylglucosamine through repetition. Hyaluronic acid is an endogenous substance of a human body and has good biocompatibility; hyaluronic acid has high viscoelasticity and non-Newtonian rheological characteristics; hyaluronic acid has the characteristics of being free of toxicity, immunogenicity and irritation, having very high safety and being capable of being degraded and eliminated through injecting hyaluronidase, thereby being extensively used as a soft tissue filler in cosmetology. That is to say, a volume of soft tissue is increased through injecting hyaluronic acid into skin, and thus, the aims of wrinkle-removing or shaping can be achieved. However, hyaluronic acid is present in the form of liquid and is very prone to decomposition under the action of in-vivo hyaluronidase and free radicals, so that a shaping effect is hard to achieve, and the filling effect duration is short.

In order to overcome this defect, people apply a crosslinking technology to hyaluronic acid, namely hyaluronic acid molecules are connected through a crosslinker to form a relatively-stable network structure, so that hyaluronic acid is not prone to decomposition anymore, and the filling duration becomes longer. Crosslinking modified sodium hyaluronate gel has the advantages of good viscoelasticity, water insolubility, high mechanical strength and long degradation time; and meanwhile, different physical characteristics are brought due to different crosslinking degrees, and thus, the sodium hyaluronate gel can better meet the requirements on cosmetology filling.

At present, crosslinkers used in commercially available sodium hyaluronate gel products mainly comprise BDDE (butanediol diglycidyl ether) and DVS (divinyl sulfone). For example, Galderma Restylane series, Allergan Juvederm series, Laboratoires Vivacy Stylage series and Hya-Dermis series all employ BDDE crosslinking to prepare the sodium hyaluronate gel; and Genzyme Hylaform series, Adoderm Varioderm series and Teoxane Teosyal series all employ the DVS as a crosslinker to prepare the sodium hyaluronate gel. Gels prepared by the two crosslinkers have entirely-different physical properties: DVS crosslinked products are hard in texture and high in crosslinking activity; and BDDE crosslinked products are soft in texture, relatively mild in reaction and high in expansion rate. It is noteworthy that the above-mentioned crosslinkers all have toxicity or potential carcinogenic hidden danger, a crosslinked space network structure plays a role in wrapping unreacted crosslinkers, and the difficulty of removal is relatively high.

In order to overcome the above-mentioned defect, in the present invention, a novel polyglycol epoxide crosslinker with low toxicity and high reaction activity and water solubility, i.e., is designed and synthesized, wherein n=4, 5, 6, 7, 8, 9, 10, 11, 12, 13, 14, 15, 16, 17, 18, 19, 20, 21, 22, 23, 24, . . . 48 . . . 200; novel crosslinked sodium hyaluronate gel is prepared by using the novel polyglycol epoxide crosslinker as a crosslinker, is soft and is good in viscoelasticity, low in toxicity and good in product uniformity; the present invention further relates to a specific preparation method of the crosslinked sodium hyaluronate gel.

SUMMARY

In order to overcome the defect in the prior art that prepared sodium hyaluronate gel cannot concurrently have the advantages of high gel degradation resistance, low crosslinker toxicity, good injectability, etc, in the present invention, a novel water-soluble crosslinker with low toxicity and high reaction activity is designed and synthesized firstly, and then, modified sodium hyaluronate gel for injection, which is low in toxicity, little in residual, small in squeezing and pushing force, good in shaping performance, good in enzyme resistance and long in in-vivo retention time, is prepared by using the crosslinker. Specifically, in order to overcome the above-mentioned defect in the prior art, in the present invention, a novel polyglycol epoxide with low toxicity and high reaction activity and water solubility, i.e., is designed and synthesized, wherein n=4, 5, 6, 7, 8, 9, 10, 11, 12, 13, 14, 15, 16, 17, 18, 19, 20, 21, 22, 23, 24, . . . , 48, . . . , 200; and novel crosslinked sodium hyaluronate gel is prepared by using the novel polyglycol epoxide crosslinker as a crosslinker, is soft and is good in viscoelasticity, low in toxicity and good in product uniformity. The present invention further relates to a specific preparation method of the crosslinked sodium hyaluronate gel. Preferably, the polyglycol or polyglycol epoxide disclosed by the present invention is a compound with single molecular weight.

In one aspect, the present invention provides a novel polyglycol epoxide with low toxicity, high reaction activity and super hydrophilicity, having a structure represented by a general formula I:

Wherein,
n is an integer of 4-200;
EPOX is wherein Y is one or more selected from —$(CR_1R_2)_m$—, —$(CH_2)_mNH$—, —$NHCO(CH_2)_m$—, —$(CH_2)_mCONH$— and —$CO(CH_2)_m$—, m is an integer of 1-10;

$R_1$ and $R_2$ are independently selected from H, alkyl, cycloalkyl, cycloalkyl alkyl, alkenyl, aryl, aralkyl, heterocyclyl, heterocyclyl alkyl, —$COR_3$, —$C(O)OR_3$, —$C(O)NR_3R_4$, —$CH=NR_3$, —CN, —$OR_3$, —$OC(O)R_3$, —$S(O)_n$—$R_3$, —$NR_3R_4$, —$NR_3C(O)R_4$ and halogen;

t is selected from 0, 1 and 2;

$R_3$ and $R_4$ each are independently selected from H, alkyl, cycloalkyl, alkenyl, aryl, heterocyclyl and halogen.

Preferably, the n is an integer of 10-100, more preferably an integer of 10-50, further preferably an integer of 12-30; or the n preferably is an integer of 10-100, more preferably an integer of 10-30, most preferably 10, 11, 12, 13, 14, 15, 16, 17, 18, 19, 20, 21, 22, 23, 24, 25, 26, 27, 28, 29 or 30.

Preferably, the Y is —$(CR_1R_2)_m$—.

Preferably, the m is an integer of 1-5, for example 1, 2, 3, 4 or 5.

In a preferred embodiment of the present invention, the m=1.

Preferably, the $R_1$ and the $R_2$ are independently selected from H, C1-C6 alkyl, C3-C6 cycloalkyl, —$OR_3$, —$NR_3R_4$ and halogen.

Preferably, the $R_3$ and the $R_4$ are independently selected from H and C1-C3 alkyl.

In a preferred embodiment of the present invention, both the $R_1$ and the $R_2$ are H.

In a more preferred embodiment of the present invention, the Y is —$CH_2$—.

The polyglycol epoxide disclosed by the present invention preferably is a compound with single molecular weight.

Preferably, the polyglycol epoxide disclosed by the present invention has a structure as follows:

Wherein, n is an integer of 4-200, preferably an integer of 10-100, more preferably an integer of 10-50, further preferably an integer of 10-30 (specifically such as 10, 11, 12, 13, 14, 15, 16, 17, 18, 19, 20, 21, 22, 23, 24, 25, 26, 27, 28, 29 or 30).

In another aspect, the present invention provides a preparation method of the polyglycol epoxide, comprising a step of catalyzing a reaction between EPOX—X and polyglycol with a catalyst in a solvent;

The polyglycol has a structure of and n is an integer of 4-200;
In the EPOX—X, —X is a leaving group;
EPOX is wherein Y is one or more selected from —$(CR_1R_2)_m$—, —$(CH_2)_mNH$—, —$NHCO(CH_2)_m$—, —$(CH_2)_mCONH$— and —$CO(CH_2)_m$—;

m is an integer of 1-10;

$R_1$ and $R_2$ are independently selected from H, alkyl, cycloalkyl, cycloalkyl alkyl, alkenyl, aryl, aralkyl, heterocyclyl, heterocyclyl alkyl, —$COR_3$, —$C(O)OR_3$, —$C(O)NR_3R_4$, —$CH=NR_3$, —CN, —$OR_3$, —$OC(O)R_3$, —$S(O)_t$—$R_3$, —$NR_3R_4$, —$NR_3C(O)R_4$ and halogen;

t is selected from 0, 1 and 2;

$R_3$ and $R_4$ each are independently selected from H, alkyl, cycloalkyl, alkenyl, aryl, heterocyclyl and halogen.

Preferably, the n is an integer of 10-100, more preferably an integer of 10-50, further preferably an integer of 12-30; or the n preferably is an integer of 10-100, more preferably an integer of 10-30, most preferably 10, 11, 12, 13, 14, 15, 16, 17, 18, 19, 20, 21, 22, 23, 24, 25, 26, 27, 28, 29 or 30.

Preferably, the —X is selected from —F, —Cl, —Br, —I, more preferably, the —X is —Cl or —Br.

In a preferred embodiment of the present invention, the Y is —$(CR_1R_2)_m$—.

Preferably, the m is an integer of 1-5, for example 1, 2, 3, 4 or 5.

In a preferred embodiment of the present invention, the m=1.

Preferably, the $R_1$ and the $R_2$ are independently selected from H, C1-C6 alkyl, C3-C6 cycloalkyl, —$OR_3$, —$NR_3R_4$ and halogen.

Preferably, the $R_3$ and the $R_4$ are independently selected from H and C1-C3 alkyl.

In a preferred embodiment of the present invention, both the $R_1$ and the $R_2$ are H.

In a more preferred embodiment of the present invention, the Y is —$CH_2$—.

Preferably, the catalyst is a base catalyst, comprises an organic base or an inorganic base and preferably comprises, but not limited to, one or more selected from pyridine, triethylamine, caesium carbonate, sodium carbonate, potassium carbonate, sodium bicarbonate, potassium bicarbonate, sodium hydroxide, potassium hydroxide, sodium alcoholate and potassium alcoholate.

Preferably, the solvent comprises, but not limited to, one or more selected from 1,4-dioxane, tetrahydrofuran, toluene, acetone, ethyl acetate, acetonitrile, N,N-dimethylformamide, dimethyl sulfoxide and water.

Preferably, in the polyglycol, a mole ratio of monohydroxyl to EPOX—X is 1:(2-10) (specifically such as 1:2, 1:3, 1:4, 1:5, 1:6, 1:7, 1:8, 1:9 or 1:10).

Preferably, the preparation method of the polyglycol epoxide further comprises a purification step; more preferably, the purification step comprises one or more of rotary evaporation, washing, extraction, molecular distillation and column separation.

In a preferred embodiment of the present invention, the preparation method comprises the following specific steps: adding polyglycol, a solvent and a catalyst into a reaction vessel, carrying out stirring, dropwise adding halogenated or sulfonated propylene oxide into the mixture, controlling a reaction temperature not to exceed 35° C., performing filtering after a reaction is completed, washing filter residues, collecting filter liquor, and purifying the collected filter liquor, thereby obtaining the polyglycol epoxide.

A general formula of the above-mentioned reaction is as follows:

The polyglycol epoxide synthesized by adopting the preparation method is relatively high in purity, and the purity is higher than 99% through HPLC detection. The polyglycol epoxide with low toxicity, high reaction activity and super hydrophilicity can be applied to crosslinking of high polymers such as natural polymers such as natural polysaccharides and proteins and synthesized polymers such as polyethylene glycol and polyvinyl alcohol.

In another aspect, the present invention provides a crosslinker comprising the polyglycol epoxide disclosed by the present invention.

The present invention further provides a high polymer crosslinked by the polyglycol epoxide.

Preferably, the high polymer may be a natural polymer or a synthesized polymer, more preferably the natural polymer such as natural polysaccharides or proteins.

Preferably, the natural polymer comprises one or more selected from starch, chitosan, chitin, cellulose, pectin, gelatin, arabic gum, casein, chitin, silk fibroin, albumin, casein, hyaluronic acid, glycogen, sericin, gellan gum, xanthan gum, guar gum, glucan, chitosan oligosaccharide, inulin, glucomannan, mannan oligosaccharide, mannan, galactan, chondroitin sulfate, dermatan sulfate, heparin, heparan sulfate, agar and derivatives thereof;

Preferably, the synthesized polymer comprises one or more selected from polyvinylpyrrolidone, polyethylene glycol, polyethylene oxide, polyvinyl alcohol, polyvinyl acetate, polylactic acid, polyglycolic acid, polyacrylic acid, polyacrylamide, polytetrahydrofuran, polybutylene oxide, polytrimethylene oxide, polymaleic anhydride, polyhydroxyethylmethacrylate, polypropylene glycol, polycaprolactone and derivatives thereof.

In a preferred embodiment of the present invention, the natural polymer is a hyaluronic acid derivative, more preferably hyaluronate, and the hyaluronate comprises one or more selected from sodium hyaluronate, potassium hyaluronate, calcium hyaluronate, magnesium hyaluronate, zinc hyaluronate, cobalt hyaluronate and ammonium tetrabutyl hyaluronate; more preferably, the natural polymer is sodium hyaluronate.

In a preferred embodiment of the present invention, a crosslinked matter is the above-mentioned polyglycol epoxide crosslinked sodium hyaluronate.

Preferably, the sodium hyaluronate has a molecular weight of 50,000 dalton to 3,000,000 dalton (specifically such as 50,000 dalton, 100,000 dalton, 500,000 dalton, 1,000,000 dalton, 1,500,000 dalton, 2,000,000 dalton, 2,500,000 dalton or 3,000,000 dalton), more preferably 300,000 dalton to 1,500,000 dalton.

Preferably, a mole ratio of the polyglycol epoxide to a polymer unit in sodium hyaluronate is 0.01-1:1 (specifically such as 0.01:1, 0.1:1, 0.2:1, 0.3:1, 0.4:1, 0.5:1 or 1.0:1).

Based on that the novel crosslinker with low toxicity and high reaction activity and water solubility is provided, the present invention further provides modified sodium hyaluronate gel for injection, which is low in toxicity, little in residual, small in squeezing and pushing force, good in shaping performance, good in enzyme resistance and long in in-vivo retention time, and a preparation method of the modified sodium hyaluronate gel.

A preparation method of the polyglycol epoxide crosslinked sodium hyaluronate comprises a step of subjecting sodium hyaluronate to a crosslinking reaction with the polyglycol epoxide disclosed by the present invention under alkaline conditions.

In an embodiment of the present invention, the step of performing the crosslinking reaction comprises the steps of dissolving the polyglycol epoxide in an alkaline solution, adding the solution with polyglycol epoxide dissolved into sodium hyaluronate powder, and performing a reaction with stirring at a temperature of 35-45° C., preferably 40° C., thereby obtaining the crosslinked sodium hyaluronate.

Preferably, a mole ratio of the polyglycol epoxide to a polymer unit in sodium hyaluronate is 0.01-1:1 (specifically such as 0.01:1, 0.1:1, 0.2:1, 0.3:1, 0.4:1, 0.5:1 or 1.0:1).

Preferably, the alkaline solution is selected from a sodium hydroxide solution, a potassium hydroxide solution and a sodium carbonate solution; in a preferred embodiment of the present invention, the alkaline solution is an aqueous solution of NaOH with a mass concentration of 0.1-10%.

Preferably, a mass ratio of the sodium hyaluronate powder to the alkaline solution is 1:5-30 (specifically such as 1:5, 1:10, 1:15, 1:20, 1:25 or 1:30).

Preferably, the sodium hyaluronate has a molecular weight of 50,000 dalton to 3,000,000 dalton (specifically such as 50,000 dalton, 100,000 dalton, 500,000 dalton, 1,000,000 dalton, 1,500,000 dalton, 2,000,000 dalton, 2,500,000 dalton or 3,000,000 dalton), more preferably 300,000 dalton to 1,500,000 dalton.

Preferably, the preparation method of the polyglycol epoxide crosslinked sodium hyaluronate further comprises a crosslinker removing step, comprising the steps of adjusting a pH value of a crosslinking reaction product to be neutral, swelling the crosslinking reaction product and washing the swelled crosslinking reaction product with a carbonate buffer solution.

In an embodiment of the present invention, the crosslinker removing step comprises the steps: adding an acid to adjust the crosslinked sodium hyaluronate to be neutral; adding a proper amount of PBS buffer solution to swell gel; and washing the crosslinked sodium hyaluronate gel with the carbonate buffer solution at a high temperature to change structures of uncrosslinked micromolecules in the gel and lower toxicity.

Preferably, the acid is hydrochloric acid, more preferably hydrochloric acid with a concentration of 0.1N-2N.

Preferably, the carbonate buffer solution has a pH of 8-9 and may be $Na_2CO_3/NaHCO_3$, $Na_2CO_3/KHCO_3$, $K_2CO_3/NaHCO_3$, $K_2CO_3/KHCO_3$, a mass concentration of carbonate is 0.02-3%.

More preferably, the crosslinker removing step further comprises a dialysis step.

The present invention further provides crosslinked sodium hyaluronate gel for injection. The crosslinked sodium hyaluronate gel for injection is obtained through sterilizing the crosslinked sodium hyaluronate gel prepared by the above-mentioned method.

Preferably, a sterilization condition is that sterilization is performed for 15 to 25 minutes in steam with a temperature of 121° C.-125° C.

In a preferred embodiment of the present invention, the preparation method of the crosslinked sodium hyaluronate gel for injection comprises the following specific steps:

Step 1: dissolving the polyglycol epoxide in an alkaline solution, adding the solution with polyglycol epoxide dissolved into sodium hyaluronate powder, and performing a reaction with stirring at a temperature of 35-45° C., preferably 40° C., thereby obtaining the crosslinked sodium hyaluronate gel;

Step 2: adding an acid to adjust the gel to be neutral;

Step 3: adding a proper amount of PBS buffer solution to swell the gel;

Step 4: washing the crosslinked sodium hyaluronate gel with the carbonate buffer solution at a high temperature to change structures of uncrosslinked micromolecules in the gel and lower toxicity;

Step 5: repeatedly performing dialysis time after time to remove a micromolecular crosslinker remaining in the gel;

Step 6: performing screening with a standard screen; and

Step 7: placing gel particles collected in the step 6 into a preparation bottle, adding a flowing phase, filling the mixture into a disposable syringe sterilized in advance, and performing sterilization for 15 to 25 minutes in steam with a temperature of 121° C.-125° C., thereby obtaining the modified sodium hyaluronate gel for injection.

The crosslinked sodium hyaluronate prepared by the method has a structural schematic diagram as follows:

Wherein, J, K and n are positive integers, the n is an integer of 4-200, and both the J and the K can be determined according to a molecular weight of the sodium hyaluronate.

The present invention further provides gel comprising the above-mentioned polyglycol epoxide crosslinked sodium hyaluronate.

The present invention further provides application of the crosslinked sodium hyaluronate in preparation of products for drugs, medical cosmetology and cosmetics.

Preferably, the application is application of the crosslinked sodium hyaluronate in preparation of products for medical cosmetology.

Preferably, the products for medical cosmetology are soft tissue fillers.

The present invention further provides a soft tissue filler comprising the crosslinked sodium hyaluronate disclosed by the present invention.

Through preparing the crosslinked sodium hyaluronate by adopting the novel crosslinker, the present invention has the beneficial effects that:

The crosslinker used in the prepared crosslinked sodium hyaluronate gel is the polyglycol epoxide; firstly, a plurality of ether bonds are present in the molecule of the polyglycol epoxide, the water solubility of the polyglycol epoxide is better than that of the traditional crosslinker BDDE, and thus, the polyglycol epoxide is more easily subjected to a crosslinking reaction with polysaccharides compared with the BDDE to produce the crosslinked sodium hyaluronate gel in case of the same mole number and the same reaction conditions; secondly, the polyglycol epoxide crosslinker is different from macromolecular polyethylene glycol and is a compound with a single molecular weight, and thus, the stability of different batches of the sodium hyaluronate gel prepared through crosslinking by adopting the polyglycol epoxide is superior to that by adopting polyethylene glycol epoxide; again, molecular chain length of the short-chain polyglycol epoxide is greater than that of the BDDE, the polyglycol epoxide may be wound with chained hyaluronic acid molecules, and thus the softness, viscoelasticity and stability of the gel are enhanced; then, polyglycol is relatively easy in adjustment of the number of repeating units and relatively easy in control of length, and thus, the gel prepared by taking the polyglycol epoxide as a crosslinker is relatively easy in regulation and control of properties; and finally, the toxicity of the polyglycol epoxide is greatly lowered compared with that of the BDDE, so that the safety of the polyglycol epoxide crosslinked sodium hyaluronate gel as a human soft tissue filler is enhanced, and adverse reactions possibly caused by toxicity of the original crosslinker BDDE are avoided.

The present invention integrates a crosslinked sodium hyaluronate gelling and impurity removing process, and the modified sodium hyaluronate gel for injection, which is low in toxicity, little in residual, small in squeezing and pushing force, good in shaping performance, good in enzyme resistance and long in in-vivo retention time, can be prepared; particularly, the present invention develops a mild crosslinker deactivation technology, and unreacted epoxide groups in the gel are subjected to a hydrolysis reaction in a carbonate buffer system with a pH of 8-9, so that the difficulty of impurity removal of the crosslinked sodium hyaluronate gel can be effectively lowered, and the problem of toxicity due to the fact that the BDDE is used in an original crosslinking method is avoided.

DETAILED DESCRIPTION OF THE EMBODIMENTS

Unless otherwise defined, all scientific and technical terms used in the present invention have meanings the same as those generally understood by technical personnel in the technical field involved in the present invention, for example: 'alkyl' means a linear or branched hydrocarbon chain free radical free of an unsaturated bond; in the present invention, C1-C6 alkyl means alkyl containing 1-6 carbon atoms, for example methyl, ethyl, n-propyl, isopropyl, n-butyl, isobutyl, tertiary butyl, n-amyl, n-hexyl, etc., preferably C1-C3 alkyl (such as methyl, ethyl, n-propyl and isopropyl); 'cycloalkyl' means an alicyclic hydrocarbon, and typical cycloalkyl contains 1 to 4 monocyclic rings and/or condensed rings and contains 3 to about 18 carbon atoms; and in the present invention, C3-C6 cycloalkyl means cycloalkyl containing 3-6 carbon atoms, such as cyclopropyl, cyclopentyl and cyclohexyl.

Technical schemes in embodiments of the present invention will be described clearly and completely below with reference to drawings in the embodiments of the present invention. Apparently, the embodiments described are only part of the embodiments of the present invention, rather than all embodiments. All other embodiments achieved by those having ordinary skill in the art on the premise of not making inventive labor on the basis of the embodiments of the present invention all fall within the protection scope of the present invention.

Embodiment 1: Synthesis of tetraethylene Glycol Diglycidyl Ether (Ia)

Synthesis of tetraethylene glycol diglycidyl ether with a structure as follows:

Tetraethylene glycol (0.1 mol), tetrahydrofuran (100 mL) and potassium hydroxide (0.4 mol) are added into a three-necked flask, stirring is performed in a water bath, then, chloroepoxy propane (0.6 mol) is dropwise added into the reaction system, the reaction temperature is controlled not to exceed 35° C., and a reaction is carried out at room temperature overnight. Reaction liquor is filtered after the reaction ends up, filter residues are washed with dichloromethane, then, the obtained filtrate is collected, and rotary evaporation is performed to remove dichloromethane, so as to obtain a crude product. The crude product is subjected to molecular distillation, thereby obtaining pure tetraethylene glycol diglycidyl ether.

$^1$H-NMR (DMSO-d6): 2.52-2.55 (m, 2H), 2.70-2.73 (m, 2H), 3.07-3.11 (m, 2H), 3.22-3.28 (m, 2H), 3.52-3.56 (m, 16H), 3.68-3.73 (m, 2H);

HPLC detection: product purity 99.6%;

Mass spectrum ESI: 329.6 [M+Na].

Embodiment 2: Synthesis of Dodecaethylene Glycol Ddiglycidyl Ether (Ib)

Synthesis of dodecaethylene glycol diglycidyl ether with a structure as follows:

Dodecaethylene glycol (0.1 mol), tetrahydrofuran (100 mL) and potassium hydroxide (0.4 mol) are added into a three-necked flask, stirring is performed in a water bath, then, chloroepoxy propane (0.6 mol) is dropwise added into the reaction system, the reaction temperature is controlled not to exceed 35° C., and a reaction is carried out at room temperature overnight. Reaction liquor is filtered after the reaction ends up, filter residues are washed with dichloromethane, then, the obtained filtrate is collected, and rotary evaporation is performed to remove dichloromethane, so as to obtain a crude product. The crude product is subjected to molecular distillation, thereby obtaining pure dodecaethylene glycol diglycidyl ether.

$^1$H-NMR (DMSO-d6): 2.51-2.55 (m, 2H), 2.70-2.73 (m, 2H), 3.07-3.11 (m, 2H), 3.22-3.29 (m, 2H), 3.51-3.57 (m, 48H), 3.68-3.73 (m, 2H);

HPLC detection: product purity 99.3%;

Mass spectrum ESI: 681.9 [M+Na].

Embodiment 3: Synthesis of Tetracosaethylene Glycol Diglycidyl Ether (Ic)

Synthesis of tetracosaethylene glycol diglycidyl ether with a structure as follows:

Ic

Tetracosaethylene glycol (0.1 mol), tetrahydrofuran (100 mL) and potassium hydroxide (0.4 mol) are added into a three-necked flask, stirring is performed in a water bath, then, chloroepoxy propane (0.6 mol) is dropwise added into the reaction system, the reaction temperature is controlled not to exceed 35° C., and a reaction is carried out at room temperature overnight. Reaction liquor is filtered after the reaction ends up, filter residues are washed with dichloromethane, then, the obtained filtrate is collected, and rotary evaporation is performed to remove dichloromethane, so as to obtain a crude product. The crude product is subjected to column separation, thereby obtaining pure tetracosaethylene glycol diglycidyl ether.

$^1$H-NMR (DMSO-d6): 2.51-2.55 (m, 2H), 2.70-2.73 (m, 2H), 3.07-3.11 (m, 2H), 3.22-3.28 (m, 2H), 3.51-3.56 (m, 96H), 3.68-3.73 (m, 2H);

HPLC detection: product purity 99.2%;

Mass spectrum MALDI-TOF: 1210.0 [M+Na].

Embodiment 4: Synthesis of PEG1000 Diglycidyl Ether (Id)

Synthesis of PEG1000 diglycidyl ether with a structure as follows:

Id

Di-HO-PEG1000-OH (0.1 mol), tetrahydrofuran (100 mL) and potassium hydroxide (0.4 mol) are added into a three-necked flask, stirring is performed in a water bath, then, chloroepoxy propane (0.6 mol) is dropwise added into the reaction system, the reaction temperature is controlled not to exceed 35° C., and a reaction is carried out at room temperature overnight. Reaction liquor is filtered after the reaction ends up, filter residues are washed with dichloromethane, then, the obtained filtrate is collected, and rotary evaporation is performed to remove dichloromethane, so as to obtain a crude product. The crude product is subjected to column separation, thereby obtaining pure PEG1000 diglycidyl ether.

$^1$H-NMR (DMSO-d6): 2.52-2.55 (m, 2H), 2.70-2.73 (m, 2H), 3.06-3.11 (m, 2H), 3.23-3.29 (m, 2H), 3.45-3.69 (m, H in —(CH2CH2O)—), 3.72-3.75 (m, 2H);

Mass spectrum MALDI-TOF: 901.8, 945.9, 989.9, 1033.9, 1078.0, 1122.0, 1166.1, 1210.1, 1245.1, 1298.2, 1342.2 [M+Na].

Embodiment 5: Tetraethylene Glycol Diglycidyl Ether Crosslinked Sodium Hyaluronate Gel (IIa)

A crosslinker, i.e., tetraethylene glycol diglycidyl ether (0.2 mol) is dissolved into a NaOH solution, the solution with the crosslinker dissolved is added into sodium hyaluronate powder (1 mol of polymeric unit), and a reaction is carried out at a temperature of 40° C. with stirring to form crosslinked sodium hyaluronate gel; secondly, a proper amount of hydrochloric acid is added into the gel to adjust pH to 7.0, and then, a proper amount of PBS buffer solution is added for gel swelling; then, the gel is screened with a standard pharmacopoeia screen, gel particles are collected, then, the crosslinked sodium hyaluronate gel is washed with a carbonate buffer solution at a high temperature; and finally, the gel is subjected to repeated dialysis, then, screening is performed with the standard pharmacopoeia screen, and compounding, filling and steam sterilizing are performed, thereby obtaining modified sodium hyaluronate gel for injection.

$^1$H-NMR (D20, NaOD): 1.80 (s, 3H), 3.26 (s, 3H), 3.41 (s, H), 3.56 [s, (HEG4+5H)], 3.79 (s, 1H), 4.33-4.36 (d, 2H).

Embodiment 6: Dodecaethylene Glycol Diglycidyl Ether Crosslinked Sodium Hyaluronate Gel (IIb)

A crosslinker, i.e., dodecaethylene glycol diglycidyl ether (0.2 mol) is dissolved into a NaOH solution, the solution with the crosslinker dissolved is added into sodium hyaluronate powder (1 mol of polymeric unit), and a reaction is carried out at a temperature of 40° C. with stirring to form crosslinked sodium hyaluronate gel; secondly, a proper amount of hydrochloric acid is added into the gel to adjust pH to 7.0, and then, a proper amount of PBS buffer solution is added for gel swelling; then, the gel is screened with a standard pharmacopoeia screen, gel particles are collected, then, the crosslinked sodium hyaluronate gel is washed with a carbonate buffer solution at a high temperature; and finally, the gel is subjected to repeated dialysis, then, screening is performed with the standard pharmacopoeia screen, and compounding, filling and steam sterilizing are performed, thereby obtaining modified sodium hyaluronate gel for injection.

$^1$H-NMR (D$_2$O, NaOD): 1.81 (s, 3H), 3.28 (s, 3H), 3.40 (s, H), 3.56 [s, (H$_{EG12}$+5H)], 3.78 (s, 1H), 4.32-4.35 (d, 2H).

Embodiment 7: Tetracosaethylene Glycol Diglycidyl Ether Crosslinked Sodium Hyaluronate Gel (IIc)

A crosslinker, i.e., tetracosaethylene glycol diglycidyl ether (0.2 mol) is dissolved into a NaOH solution, the solution with the crosslinker dissolved is added into sodium hyaluronate powder (1 mol of polymeric unit), and a reaction is carried out at a temperature of 40° C. with stirring to form crosslinked sodium hyaluronate gel; secondly, a proper amount of hydrochloric acid is added into the gel to adjust pH to 7.0, and then, a proper amount of PBS buffer solution is added for gel swelling; then, the gel is screened with a standard pharmacopoeia screen, gel particles are collected, then, the crosslinked sodium hyaluronate gel is washed with a carbonate buffer solution at a high temperature; and finally, the gel is subjected to repeated dialysis, then, screening is performed with the standard pharmacopoeia screen, and compounding, filling and steam sterilizing are performed, thereby obtaining modified sodium hyaluronate gel for injection.

$^1$H-NMR (D$_2$O, NaOD): 1.80 (s, 3H), 3.27 (s, 3H), 3.40 (s, H), 3.56 [s, (H$_{EG24}$+5H)], 3.79 (s, 1H), 4.32-4.36 (d, 2H).

Embodiment 8: PEG1000 Diglycidyl Ether Crosslinked Sodium Hyaluronate Gel (IId)

A crosslinker, i.e., PEG1000 diglycidyl ether (0.2 mol) is dissolved into a NaOH solution, the solution with the crosslinker dissolved is added into sodium hyaluronate powder (1 mol of polymeric unit), and a reaction is carried out at a temperature of 40° C. with stirring to form crosslinked sodium hyaluronate gel; secondly, a proper amount of hydrochloric acid is added into the gel to adjust pH to 7.0, and then, a proper amount of PBS buffer solution is added for gel swelling; then, the gel is screened with a standard pharmacopoeia screen, gel particles are collected, then, the crosslinked sodium hyaluronate gel is washed with a carbonate buffer solution at a high temperature; and finally, the gel is subjected to repeated dialysis, then, screening is performed with the standard pharmacopoeia screen, and compounding, filling and steam sterilizing are performed, thereby obtaining modified sodium hyaluronate gel for injection.

$^1$H-NMR (D$_2$O, NaOD): 1.80 (s, 3H), 3.26 (s, 3H), 3.41 (s, H), 3.55 [s, (H$_{PEG1000}$+5H)], 3.80 (s, 1H), 4.32-4.35 (d, 2H).

Embodiment 9: Cytotoxicity Experiment

A cytotoxicity experiment is achieved through detecting the propagation rate of cells referring to standards for biological evaluation-in vitro cell toxicity test of medical instruments. In the experiment, an extraction method is adopted, a cell toxicity test is performed by adopting cells L929, a relative growth rate (RCR) of the cells is calculated through assaying the absorbance value by using an enzyme-linked immunoassay instrument, and the higher the RCR, the better the biocompatibility and the lower the toxicity. By taking BDDE as a control, cytotoxicity test results of polyglycol diglycidyl ether crosslinkers prepared in embodiments 1-4 are shown in a table 1; meanwhile, median inhibitory concentrations of crosslinker compounds (polyglycidyl ether prepared in embodiments 1-3 and BDDE) are tested by adopting the cells L929, and experimental results are shown in a table 2; and moreover, by taking BDDE crosslinked sodium hyaluronate gel (BDDE-HA) as a control, cytotoxicity test results of polyglycol diglycidyl ether crosslinked sodium hyaluronate gel prepared in embodiments 5-8 are shown in a table 3.

TABLE 1

Cytotoxicity test results of polyglycol diglycidyl ether crosslinkers

| Test Group | Ia | Ib | Ic | Id | BDDE |
|---|---|---|---|---|---|
| RCR | 62% | 89% | 89% | 87% | 30% |

TABLE 2

Test results of median inhibitory concentrations (IC50) of polyglycidyl ether and BDDE

| Test Group | Compound | Cell line | IC50 (µM) |
|---|---|---|---|
| 1 | Ia | L929 | 127.3 |
| 2 | Ib | L929 | 2303 |
| 3 | Ic | L929 | 1883 |
| 4 | BDDE | L929 | 97.95 |

TABLE 3

Cytotoxicity test results of polyglycol diglycidyl ether crosslinked sodium hyaluronate gel

| Test Group | IIa | IIb | IIc | IId | BDDE-HA |
|---|---|---|---|---|---|
| RCR | 88% | 91% | 92% | 89% | 85% |

Seen from the table 1 and the table 2, the biocompatibility of the polyglycol diglycidyl ether crosslinkers is obviously superior to that of the BDDE; and seen from the table 3, the biocompatibility of the polyglycol diglycidyl ether crosslinked sodium hyaluronate gel is superior.

Embodiment 10: Squeezing and Pushing Force Experiment

Figure 1:
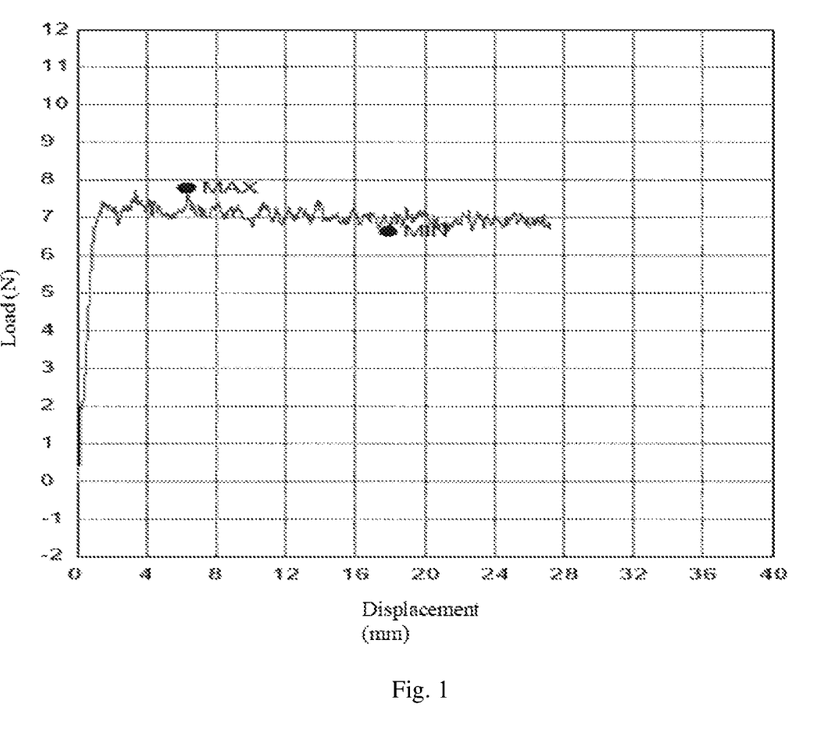
FIG. 1 is a squeezing and pushing force curve of dodecaethylene glycol diglycidyl ether crosslinked sodium hyaluronate gel provided in embodiment 10 of the present invention.
Figure 2:
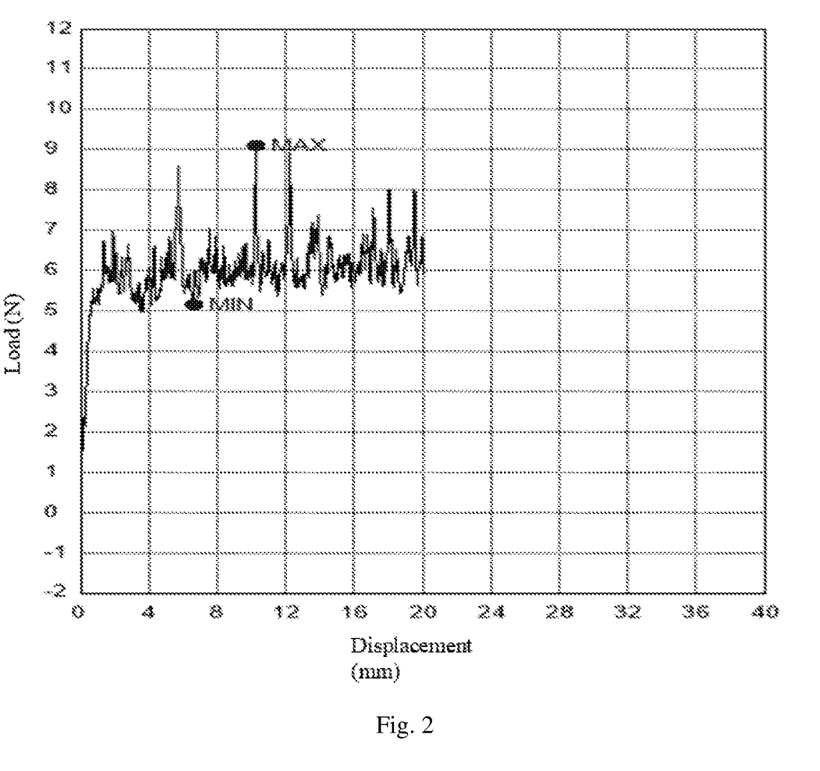
FIG. 2 is a squeezing and pushing force curve of polyethylene glycol PEG1000 diglycidyl ether crosslinked sodium hyaluronate gel provided in embodiment 10 of the present invention.

The condition of the crosslinked sodium hyaluronate gel during actual use is understood as one of indexes of evaluation on the product quality through a squeezing and pushing force experiment by using a multi-purpose mechanical tester. In the present invention, a pushing rod is pushed at a constant speed of 30 mm/min, and a sample in a syringe is squeezed out by a syringe needle of 29G to obtain a squeezing and pushing force curve, so that changes of a squeezing and pushing force of the sample during squeezing can be seen. The sample is easily squeezed out if the squeezing and pushing force is small, and the sample is not easily squeezed out if the squeezing and pushing force is large; in addition, if the size difference of the squeezing and pushing force is large, the condition that the sample is subjected to a non-uniform dispersion or gathered concentration phenomenon is shown, and the applicability during injection will be affected. A table 4 records change conditions of the squeezing and pushing force during gel squeezing and pushing, experimental data of the squeezing and pushing force of the dodecaethylene glycol diglycidyl ether crosslinked sodium hyaluronate gel are shown in FIG. 1, and a squeezing and pushing force curve is relatively smooth, which indicates that the gel is relatively homogeneous; experimental data of the squeezing and pushing force of the polyethylene glycol PEG1000 diglycidyl ether crosslinked sodium hyaluronate gel with a high molecular weight are shown in FIG. 2, and a squeezing and pushing force curve is relatively large in fluctuation, which indicates that the gel is relatively poor in homogeneity.

TABLE 4

Test results of squeezing and pushing force of polyglycol diglycidyl ether crosslinked sodium hyaluronate gel

| Test Group | IIa | IIb | IIc | IId | BDDE-HA |
|---|---|---|---|---|---|
| Squeezing and pushing force | 7-8N | 7-8N | 8-9N | 5-9N | 7-8N |

Embodiment 11: In-Vitro Enzymolysis Stability Experiment 0.5 g of crosslinked sodium hyaluronate gel is taken, 2 mL of 300 U/mL hyaluronidase solution is added, heat-preserving degradation is performed for 40 hours at a temperature of 37° C., PBS is added until a volume is 5 mL, 1 mL of the mixture is taken, 4 mL of anhydrous ethanol is added, centrifugation is performed for 15 min at a revolving speed of 10,000 r/min, 2 mL of supernatant is taken, and volume metering is performed with PBS until the volume is 5 mL to obtain a solution I; additionally, 0.5 g of crosslinked sodium hyaluronate gel is taken, 10 mL of 0.5 mol/L sulfuric acid solution is added, hydrolysis is performed in a boiling water bath for 15 min, and dilution is performed with water until a volume is 100 mL to obtain a solution II. 1 mL of solution I and 1 mL of solution II are separately taken, and the glucuronic acid content is measured by an improved carbazole development process. In-vitro enzyme degradation resistance of the gel is represented by a coefficient R, R=1−0.625A/B, wherein A represents the glucuronic acid content of the solution I, and B represents the glucuronic acid content of the solution II. The higher the R value, the better the in-vitro enzyme degradation resistance, and the more stable the crosslinked gel. Test results are shown in a table 5.

TABLE 5

Test results of in-vitro enzymolysis stability of polyglycol diglycidyl ether crosslinked sodium hyaluronate gel

| Test Group | IIa | IIb | IIc | IId | BDDE-HA |
|---|---|---|---|---|---|
| Enzyme degradation resisting coefficient | 78% | 82% | 81% | 69% | 71% |

The above embodiments are only the preferred embodiments of the present invention and not intended to limit the present invention, and any modification, equivalent replacement and the like made within the spirit and principle of the present invention shall fall within the scope of protection of the present invention.

The invention claimed is:

1. A preparation method of a biocompatible polyglycol epoxide, comprising a step of catalyzing a reaction between EPOX—X and polyglycol with a catalyst in a solvent; the polyglycol has a structure of and n is an integer of 10-30;
in the EPOX—X, —X is Cl;
EPOX is wherein Y is $(CR_1R_2)_m$;
m is 1;
$R_1$ and $R_2$ are H, wherein each of the polyglycol epoxide is a compound with single molecular weight and the biocompatiblity of the polyglycol epoxide is obtained by detecting a lower cytotoxicity than those of lower molecular weight.

2. The preparation method according to claim 1, wherein the method is characterized in that the n is one of 10, 11, 12, 13, 14, 15, 16, 17, 18, 19, 20, 21, 22, 23, 24, 25, 26, 27, 28, 29 or 30;
and/or,
the catalyst is an inorganic base.

3. The preparation method according to claim 2, wherein the method is characterized in that the catalyst comprises sodium carbonate or potassium carbonate; and/or,
the solvent comprises one or more agents selected from the group consisting of 1,4-dioxane, tetrahydrofuran, toluene, acetone, ethyl acetate, acetonitrile, N,N-dimethylformamide, dimethyl sulfoxide and water; and/or,
a mole ratio of mono-hydroxyl on the polyglycol to EPOX—X is 1: (2-10).

* * * * *